US010494165B2

(12) United States Patent
Sterns et al.

(10) Patent No.: US 10,494,165 B2
(45) Date of Patent: Dec. 3, 2019

(54) MEDICATION EVENT MONITORING SYSTEM

(71) Applicants: Kent State University, Kent, OH (US); iRxReminder LLC, Akron, OH (US)

(72) Inventors: Anthony Sterns, Akron, OH (US); Joel Hughes, Kent, OH (US); Nick Mastandrea, Chesterland, OH (US); Joshua Smith, Akron, OH (US)

(73) Assignees: KENT STATE UNIVERSITY, Kent, OH (US); IRXREMINDER, LLC, Akron ( * ) Notice: Subject to any disclaimer, the term of this patent is extended or adjusted under 35 U.S.C. 154(b) by 1013 days.

(21) Appl. No.: 14/357,052

(22) PCT Filed: Nov. 12, 2012

(86) PCT No.: PCT/US2012/064646
§ 371 (c)(1),
(2) Date: May 8, 2014

(87) PCT Pub. No.: WO2013/071225
PCT Pub. Date: May 16, 2013

(65) Prior Publication Data
US 2014/0372144 A1    Dec. 18, 2014

Related U.S. Application Data (60) Provisional application No. 61/558,134, filed on Nov. 10, 2011.

(51) Int. Cl.
*B65D 83/04*    (2006.01)
*G06F 19/00*    (2018.01)

(52) U.S. Cl.
CPC ......... *B65D 83/04* (2013.01); *G06F 19/3418* (2013.01); *G06F 19/3462* (2013.01)

(58) Field of Classification Search
CPC ......... G06Q 50/22; G06Q 50/24; B65D 83/04
(Continued)

(56) References Cited

U.S. PATENT DOCUMENTS 4,809,877 A * 3/1989 Albright ............... A61J 7/0481
221/121
4,990,948 A    2/1991 Sasaki et al.
(Continued)

FOREIGN PATENT DOCUMENTS

WO    WO 2003/044755 A1    5/2003

*Primary Examiner* — Jonathan Ng
(74) *Attorney, Agent, or Firm* — Renner Kenner Greive Bobak Taylor & Weber (57) ABSTRACT

A medication and event monitoring system operates through the internet, interconnecting and accommodating the transfer of information and data between a patient center, a caregiver/researcher center, and a pharmacist. A control center is provided in intercommunication with the patient, caregiver and pharmacist for accommodating the exchange of information and data regarding medication usage between and among the persons of interest. The patient center also includes physical sensing devices, such as for blood pressure, temperature, and the like for obtaining and transmitting information. The patient communicates through a smartphone, and further communicates through pill dispensing devices housed in a docking system that is in intercommunication with the various centers. The pill dispensing devices accommodate pills of various sizes and shapes, are easily used by a patient, and have associated sensing and recording devices for ensuring that the medication is taken in the appropriate quantities and at the appropriate time.

3 Claims, 8 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 6,150,942 A | 11/2000 | O'Brien | |
| 7,028,723 B1* | 4/2006 | Alouani | B65B 5/101 141/83 |
| 8,494,880 B2* | 7/2013 | Tripoli | G06Q 10/00 705/2 |
| 8,666,543 B2* | 3/2014 | MacVittie | B65D 83/0409 221/241 |
| 9,218,458 B2* | 12/2015 | Baarman | A61J 7/0084 |
| 9,323,897 B2* | 4/2016 | Horst | G07F 17/0092 |
| 2006/0102646 A1 | 5/2006 | Godlewski | |
| 2006/0218014 A1* | 9/2006 | Walker | G06F 19/3462 705/3 |
| 2006/0283876 A1* | 12/2006 | Mocnik | A61J 7/0409 221/300 |
| 2008/0179387 A1 | 7/2008 | Cantlay et al. | |
| 2009/0259486 A1* | 10/2009 | Burg | G06F 19/3418 705/2 |
| 2009/0281657 A1* | 11/2009 | Gak | A61J 7/0481 700/242 |
| 2010/0013597 A1* | 1/2010 | Determan | G07C 9/00563 340/5.82 |
| 2010/0036681 A1 | 2/2010 | Naik et al. | |
| 2010/0168525 A1* | 7/2010 | Hyde | A61B 5/0484 600/300 |
| 2010/0228566 A1 | 9/2010 | Taylor et al. | |
| 2010/0305749 A1* | 12/2010 | Coe | A61J 7/0481 700/231 |

* cited by examiner

MEDICATION EVENT MONITORING SYSTEM

This application claims the benefit of U.S. Patent Application No. 61/558,134, for "Medication Adherence System," filed Nov. 10, 2011, incorporated fully herein by reference.

TECHNICAL FIELD

The invention herein resides in the art of apparatus and techniques for monitoring, recording, manipulating and using data corresponding to events associated with the taking of medication and/or the wellbeing of an individual. More particularly, the invention relates to a system that accommodates the communication of data and/or the transfer of medication between and among an individual or patient, in the first instance, a researcher or caregiver in a second instance, and a pharmacist in the third instance. Particularly, the invention resides in the art of compliance systems and apparatus to ensure the proper care and treatment of an individual and/or the acquisition of data from the behavior and activities of that individual in order to ensure compliance with a protocol for ensuring the wellbeing of the individual.

BACKGROUND OF THE INVENTION

The wellbeing of individuals, whether patients or other otherwise, is often dependent upon the ability to access data regarding such individual pertaining to his/her activities and undertakings, and particularly with regard to their compliance in the administering of medication, monitoring of symptoms, and carrying out prescribed activities to maintain wellness. Adherence to medication protocols is a known issue in the medical field, it being estimated that less than 60% of patients correctly adhere to medication instructions and schedules. Consequently, a variety of devices and products have been developed and introduced commercially with the intent and desire of improving adherence to such protocols.

In the past, pillboxes having separate compartments for the days of the week or month are marketed to patients taking multiple medications daily. In addition, a number of "alarm" or "nagging" type devices are available, which provide an audible and/or visual alarm as a reminder to take medications. A small number of recent devices have compartments that are aware of being opened and report to a web service.

While the known systems provide some improvement over protocol adherence, these devices suffer from a number of shortcomings. Specifically, these known devices do not keep records of if and when medications have been taken, nor do they provide real time reminders. Additionally, known systems are not readily portable and, to the extent audible or visual alarms are used throughout the day, they are typically annoying and undesirable. They are limited in the number of pills and a small number of days that the device can support adherence.

The prior art is also devoid of systems that provide for a broad range of monitoring of the activities and/or physical indicia of an individual's wellbeing over a course of time. These systems do not provide for real time data access by the individual or patient, his physician or associated researcher, or the pharmacy providing the requested medications. The systems do not provide interaction between healthcare provider and researcher, facilitate education opportunities, serve as a hub for biometric information obtained from other devices (e.g. scales, oximeters, blood press cuffs, etc.) or provide easy modifications to existing regimens by the health care team.

In light of the foregoing, there remains a need in the art for a user friendly adaptive system capable of not only ensuring compliance to medication protocols, but also for monitoring the various indicia of the health and wellbeing of a patient or other individual over a course of time, such that data is available for either immediate or subsequent analysis and resultant modification of medication protocol if such is indicated. Further, the system can serve as an active monitor for physical parameters, activity, emotion, mood,

SUMMARY OF THE INVENTION

In light of the foregoing, embodiments of the invention contemplate the employment of a system that allows for intercommunication between and among researchers, caregivers, health care professionals, mental health professionals, specialists, pharmacists, and patients or persons of interest.

The various embodiments contemplated by the invention also contemplate the employment of the use of personal electronic devices such as smart phones to allow for communication with a patient or individual of concern with regard to various aspects of that individual's wellbeing, including the proper and timely taking of medications.

Embodiments of the invention further contemplate the use of personal dispensing devices, allowing for a monitored dispensing of medication, which devices are received and maintained in a docking system further adapted for communication with the individual's personal electronic device, smart phone or the like.

The foregoing and other aspects of the embodiment under consideration are achieved by a medication event monitoring system, comprising: a patient center; a care giver center; a pharmacy center; and a control center in intercommunication with said patient center, care giver center and pharmacy center, said control center exchanging information and data therebetween regarding medication usage.

Other aspects of various embodiments under consideration are attained by a pill dispensing device, comprising: a housing defining a cavity therein; a dispensing aperture in said housing and in selective communication with said cavity; an inner ring received within said cavity, said inner ring being selectively rotatable for effecting communication between said cavity and said dispensing aperture.

Still other aspects of various embodiments under consideration are attained by a method of ensuring compliance of a patient with a medication schedule, comprising: loading a docking system with an assortment of pill dispensing devices, said docking system being operatively connected to a communication device; signaling to a patient through said communication device that a particular medication associated with at least one of said pill dispensing devices needs to taken by the patient; activating said at least one pill dispensing device to dispense an appropriate dosage of the particular medication; and sensing the act of dispensing an appropriate dosage of the particular medication and recording such event.

DESCRIPTION OF DRAWINGS

For a complete understanding of the various embodiments and concepts disclosed herein, reference should be made to the following detailed description and accompanying drawings wherein.

DETAILED DESCRIPTION OF PREFERRED EMBODIMENTS

Figure 1:
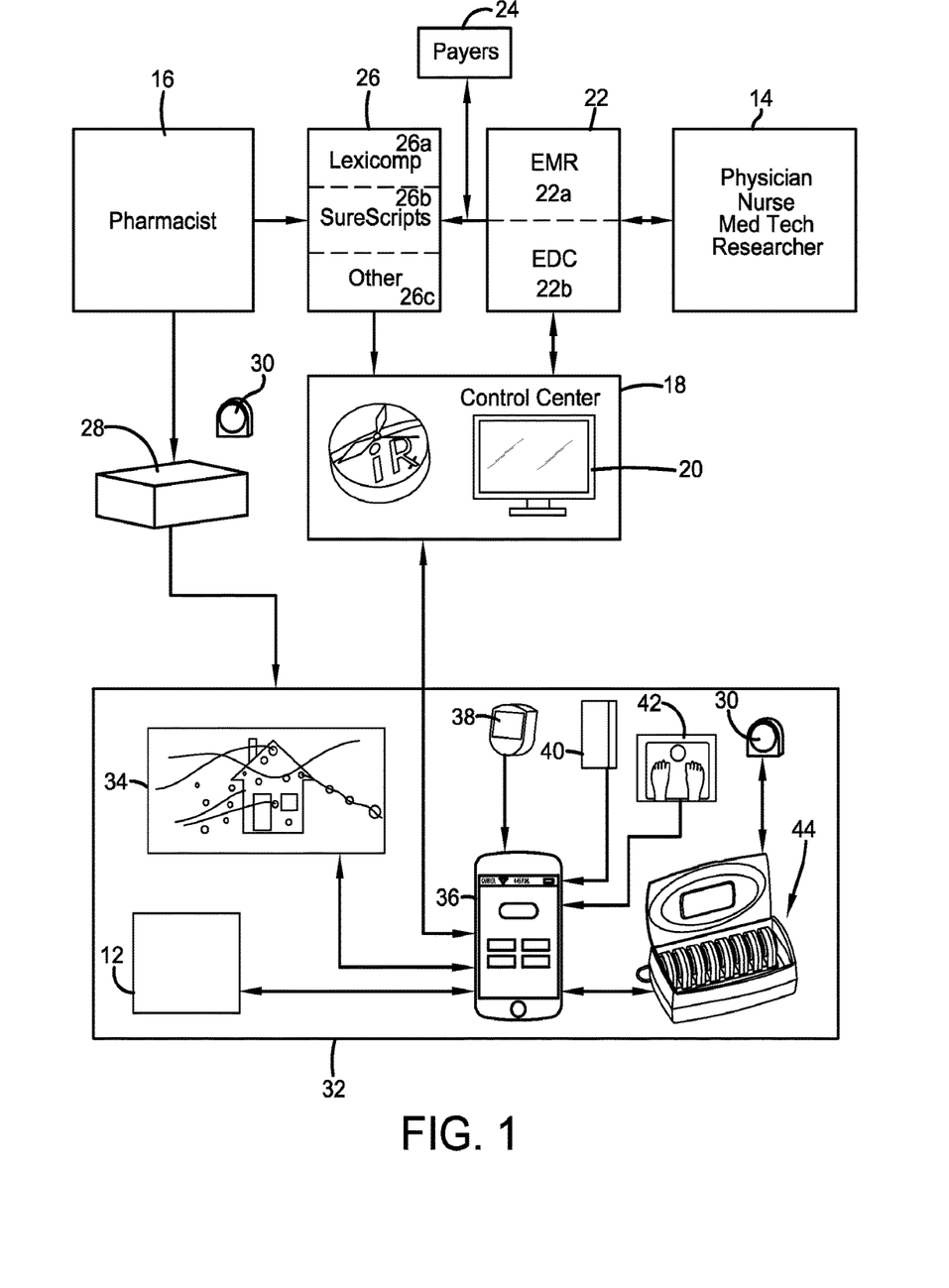
FIG. 1 is a functional block diagram of a medication event monitoring system made in accordance with an embodiment of the invention.

Referring now to the drawings and more particularly FIG. 1, it can be seen that a medication event monitoring system is designated generally by the numeral 10. The monitoring system 10 monitors, acquires data from, and provides intercommunication between three sets of individuals, including a patient or other individual 12, a healthcare provider such as a physician, nurse, or medical technician on the one hand, or a researcher on the other, all designated generally by the numeral 14. It will be appreciated herein that a purpose of the medication event monitoring system 10 is multi-faceted. In one application, a healthcare provider 14 may prescribe, monitor, and appropriately amend care provisions for a patient, or a researcher may monitor an individual as to activities, general health indicia, and the like for purposes of acquiring data for future assessment. A third type of individual includes a pharmacist 16 who, in somewhat standard fashion, issues medication at the direction and request of a healthcare provider or researcher 14.

Central to the medication event monitoring system 10 is a control center 18, typically accessed through the Internet on the "cloud," and comprising a dedicated microprocessor, personal computer 20, central computer or the like. The control center 18 is in communication with the patient or other individual 12, caregiver or researcher 14, and pharmacist 16, as shown.

A record and data system 22 is in intercommunication between the caregiver/researcher 14 and control center 18. Included in the system 22 is an electronic medical records system 22a for communication with caregivers such as physicians, nurses, medical technicians and the like, and an electronic data center 22b adapted for implementation with researchers. The record and data system 22 is configured to contain medical records of the associated patient or individual 12 for access as needed by the caregivers and researchers 14.

Also included in the system 10 is an array of "payers" such an insurance companies, governmental agencies such as Medicare and Medicaid, research organizations and the like. These entities are granted access in the system 10 for purposes of gathering information, authorizing treatment or processes, and the like.

In direct communication with the pharmacist 16 are several pharmaceutical service providers 26, including a section 26a for providing electronic data regarding drugs and medications; a section 26b comprising a virtual pharmacy control system; and a section 26c, of any of various natures for adapting and regulating the communication of the pharmacist 16 to the control center 18 or the like.

In accordance with the concepts of embodiments of the invention, the pharmacist 16 will typically package the medications for a particular patient or individual in a pill dispensing device 30, to be discussed in detail later herein. These pill dispensing devices 30 are packaged for delivery as at 28 to a patient center 32 or other location for an individual of interest. Included as a portion of the patient center 32 may be a smart house 34, termed such for including a multiplicity of sensors and detectors throughout, for monitoring a host of activities of the inhabitant, such as the patient or other individual 12. Motion sensors, activity sensors, behavior monitors, and the like may be of interest to the caregiver or researcher 14 and are present within the smart house 34. By way of example only, there may be a sensor on the stove to detect whether it has been turned on or not, at a toilet to see if it has been used, at certain light switches to see if they have been activated, at a stairway to determine access, and the like.

Also included as part and parcel of the patient center 32 is a personal electronic device such as a smart phone 36, which serves as the heart of the communication system for the patient center 32. Typically, the smart phone 36 is unique to the patient or individual 12 and the smart house 34, receiving input from the sensors of the smart house 34 and from the patient 12. The smart phone 36 is in intercommunication with the control center 18, as shown.

Also provided in data communication with the smart phone or personal electronic device 36 are a plurality of other devices which may be unique to monitoring the wellbeing of the individual or patient 12. By way of example only, a glucometer 38 may be employed particularly for patients who may be diabetic. An active graph 40, such as a pedometer or the like may be employed to monitor ambulatory activity or other movement of the patient 12. A set of scales 42 for measuring weight may similarly be provided. By way of a example, a patient's mood may be monitored by means of surveying utilizing the survey capabilities of the monitoring system and further interpreted in combination with other activities mentioned above. When changes in monitoring exceed a specified criteria on any of the physical, emotional, attitudinal, or environmental changes an alert can be sent to persons who can react, including researchers, caregivers, first responders, and healthcare professionals.

Of particular interest to the embodiments of the invention is the provision of a docking system 44, adapted for receipt and communication with one or more pill dispensing devices 30 as issued by the pharmacist 16 to the patient or other individual 12. The docking system 44 may also receive and directly communicate with the smart phone or other personal electronics device 36. It may also include self contained microchips, processors, a display screen, or the like, all of which will become apparent later herein.

Figure 2:
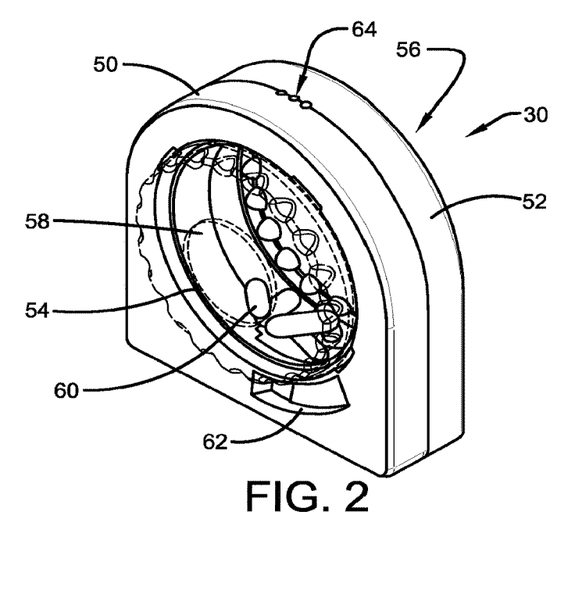
FIG. 2 is a perspective view of a personal dispensing device in accordance with an embodiment of the invention.

Referring now to FIG. 2, an appreciation can be obtained with regard to the nature and structure of the pill dispensing device 30 used in association with embodiments of the invention. As shown, a pair of mating housing haves 50, 52, preferably having clear windows or side caps 56, 58 on opposite ends thereof, are fitted together to define interiorly a cavity 59 to receive an appropriate account of pills 60 through deposit by the pharmacist 16. At the bottom of a front side of the personal dispensing device 30 is a staging region and dispensing aperture 62, accommodating the singular dispensing of pills 16 from the cavity 58. As will be apparent below, a pill 60 is first moved to the staging region through which it can be viewed through a clear plastic window, and thence subsequently through the dispensing aperture to the patient 12.

Also included as a part of the housing defined by the halves 50, 52 are apertures 64 for receiving and maintaining various means of indicia, such as light emitting diodes (LED's) 64 or the like.

Figure 3:
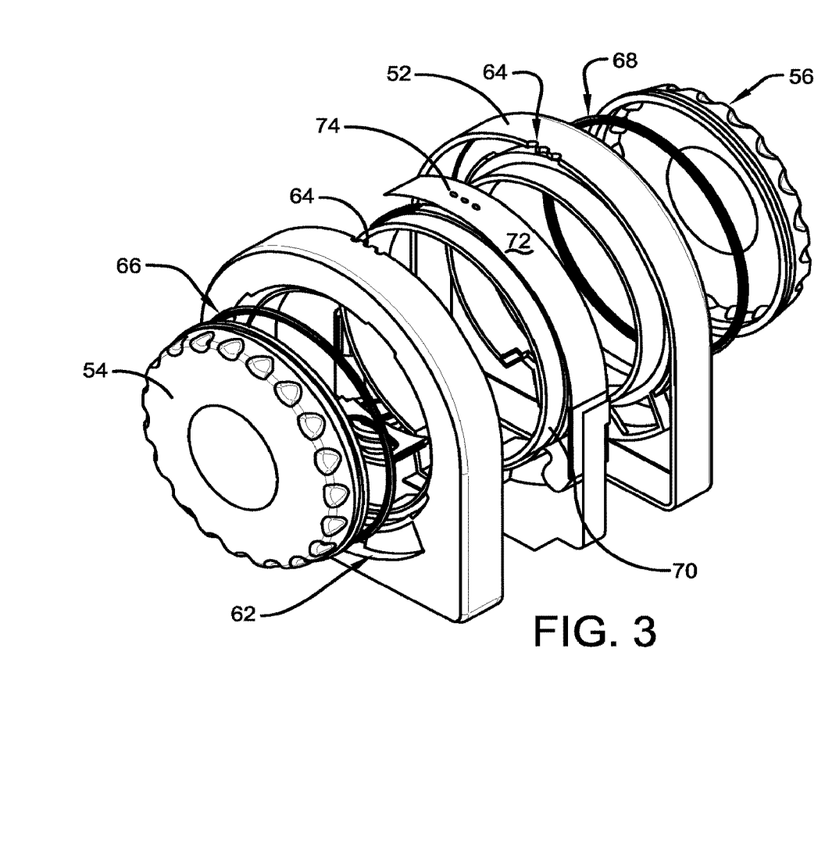
FIG. 3 is an assembly diagram of the personal dispensing device of FIG. 2 taken from a first angle.
Figures 4, 5A:
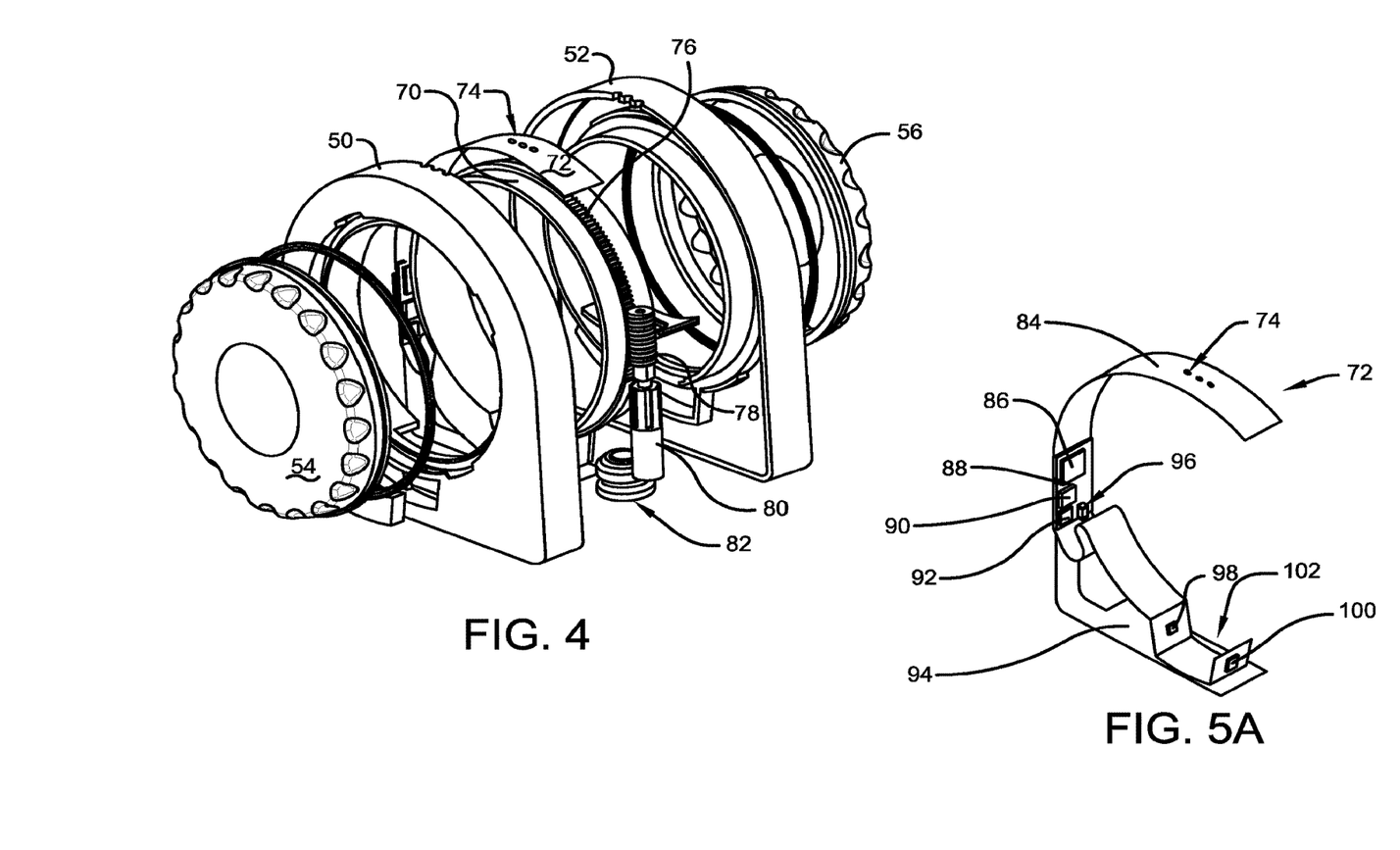
FIG. 4 is an assembly diagram of the personal dispensing device of FIG. 2, taken from an angle opposite that of FIG. 3.
FIG. 5A is perspective view of a flexible circuit band assembly of embodiments of the invention.

As shown in the assembly diagrams of FIGS. 3 and 4, respective seals 66, 68 are interposed between respective windows or side caps 54, 56 and mating housing halves 50, 52. Maintained within the housing defined by the mated housing halves 50, 52 is an inner ring 70, adapted for limited reciprocating rotation, as will become apparent below. A flexible circuit band assembly 72 receives the inner ring 70 and maintains thereon a plurality of light emitting diodes 74, for selective illumination through an associated aperture 64.

The inner ring 70 is characterized by a gear tooth ring 76 extending partially around a circumferential sector thereof. A worm gear drive 78 is in operative engagement with the gear teeth 76 and is operatively driven by a reversible DC motor 80, powered by an appropriate battery 82.

As shown in FIG. 5, the flexible circuit band assembly 72 includes a flexible circuit band 84 carrying a transceiver/microcontroller or chip 86. It also carries a temperature sensor magnetometer 88, a gyroscope 90, and an accelerometer 92. Also included as part and parcel of the flexible circuit band assembly 72 is a capacitive sensor and near field communication antenna 94. A chip antenna 96 is also provided, both being adapted for communications within the system 10.

A light source 98 is positioned across from a photo detector or photo diode 100, spanning a dispensing chamber 102, for sensing the presence or absence of the next pill to be dispensed from this staging area.

Figure 5B:
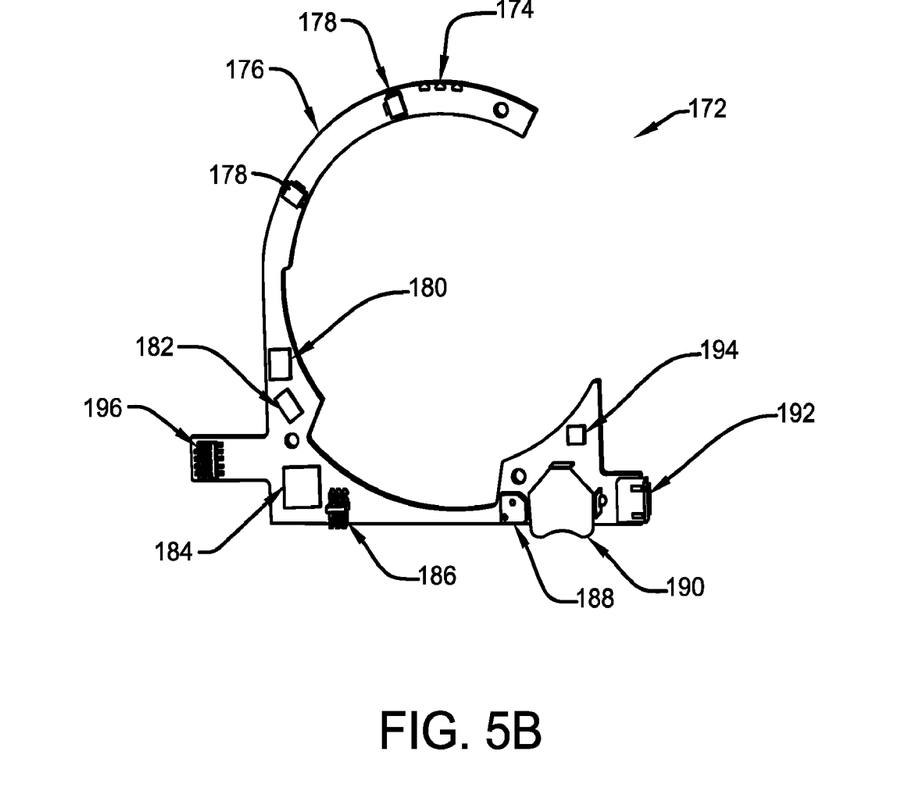
FIG. 5B is a perspective view of an arcuate rigid circuit board assembly of embodiments of the invention.

With reference now to FIG. 5B, it can be appreciated that the flexible circuit band 84, in operative association with the inner ring 70, may be replaced with a rigid circuit board assembly 172, for receipt of the inner ring 70. The rigid circuit board assembly 172 again receives a plurality of light emitting diodes 174 in a rigid arcuate printed circuit board 176. In this embodiment, limit switches 178 are mounted to the printed circuit board 176 and are adapted for selective actuation by the inner ring 70. In this embodiment, the inner ring 70 is provided with a protrusion or the like (not shown) that engages a first of the limit switches 178 when rotating in the clockwise direction, and the other when rotating in the counterclockwise direction. The outputs of the limit switches 178 signal the end of rotation in the associated direction, ensuring that when rotation commences again, it does so in the opposite direction. Accordingly, the inner ring 70 is restricted to a sector of rotation defined by the spacing between the limit switches 178.

Also mounted to the rigid printed circuit board 176 is a combination accelerometer and gyroscope, operating in similar fashion to the prior embodiment of FIG. 5A. Specifically, the accelerometer presents an output corresponding to linear motion, while the gyroscope presents an output corresponding to an angular rate of motion or rotation. This embodiment further contemplates the implementation, if desired, of a magnetometer as in the prior embodiment, the magnetometer sensing the flux density of the earth's magnetic field and, accordingly, detecting a change in orientation of the associated pill dispensing device 30. An appropriate connector 182 may be employed to interconnect various portions of the rigid circuit board assembly 172 to other circuits, whether on or off the rigid printed circuit board assembly 176.

A microcontroller or chip 184 is also provided, in association with a connector 186. Further included in attachment to the rigid printed circuit board 176 is an audible buzzer 188, which may be employed for purposes of audibly advising the user or patient 12 of either an event or a need for a timed event.

The motor 80 is again powered by a battery 82, appropriately received in a battery holder 190, affixed to the board 176. A USB connector 192 for the motor 80 is also provided, as is a motor drive circuit 194. Also shown is a programming connector 196, which is typically used only for a prototype device, for initial programming. However, the connector 196 may also be employed on standard units where customization or augmentation is desired.

Figure 6:
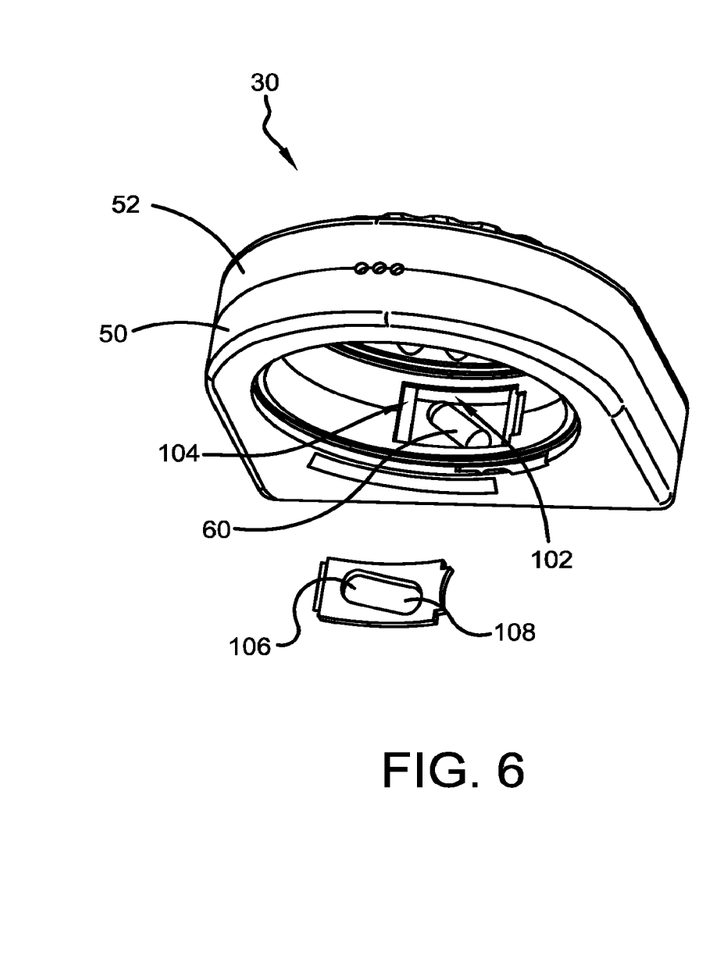
FIG. 6 is a perspective view of a personal dispensing device showing a pill dispensing template removed from an aperture and exposing a dispensing chamber.
Figure 7:
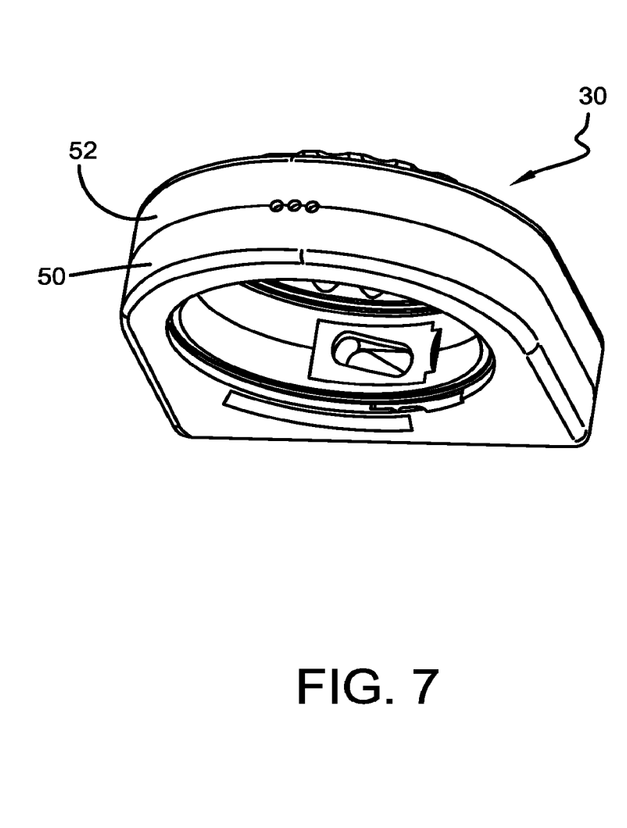
FIG. 7 is a perspective view of the personal dispensing device of FIG. 6, with the pill dispensing template in place.

As shown in FIGS. 6 and 7, the dispensing chamber 102 is positioned below an aperture 104 formed by the mating housing halves 50, 52, providing a passage for pills from the cavity 58 to a staging region and dispensing aperture 62. As mentioned above, a portion of the region 62 defining a staging area is covered by a clear window, while the remaining portion is open for the actual dispensing of a pill there through.

A dispensing template 106 is provided for receipt by the aperture 104 and is characterized by an opening 108 configured to receive and pass a pill 60. In this regard, the dispensing chamber 102 is sized and configured to receive a single pill 60.

Figure 8:
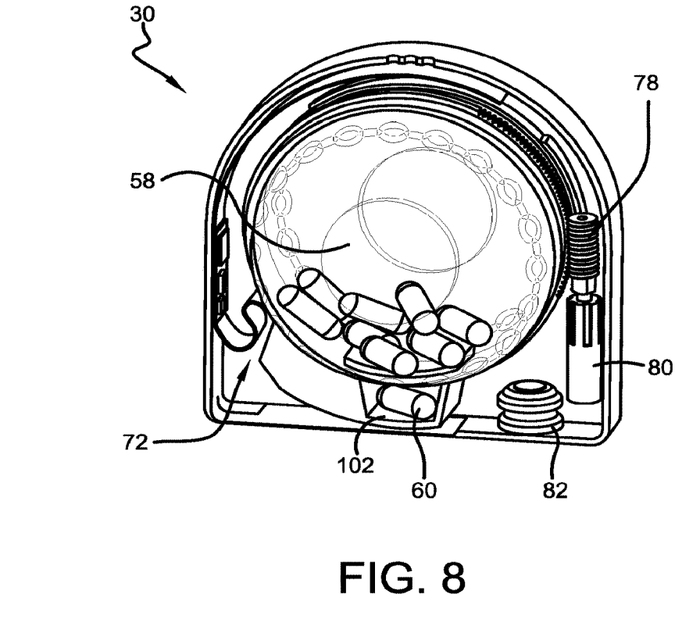
FIG. 8 is an illustrative illustration of the personal dispensing device of an embodiment of the invention, showing the staging of a pill for dispensing.
Figure 9:
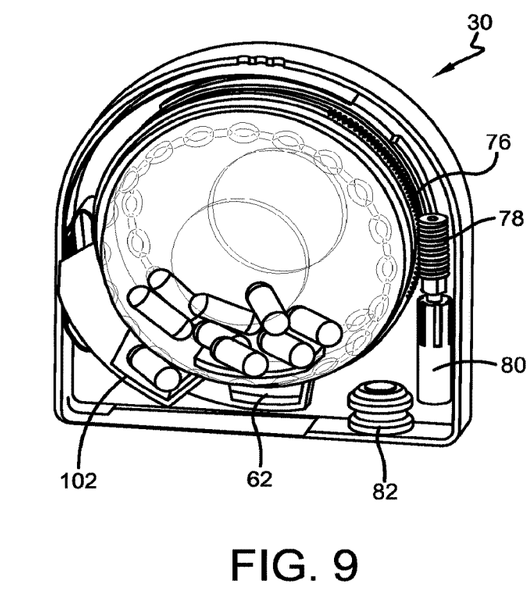
FIG. 9 is an illustrative view of the personal dispensing device of FIG. 8, showing a pill in the dispensing position.

With reference now to FIGS. 8 and 9, these illustrations show the process by which a pill 60 may be dispensed from the cavity 58 of the pill dispensing device 30 by manipulation through the reversible DC motor 80 and worm gear drive 78. As shown in the cut-away view of FIG. 8, a pill 60 has been deposited into the dispensing chamber 102 of the flexible circuit band assembly 72 by having passed through the opening 108 of the dispensing template 106. The pill 60 is then in a staging area, where it can be viewed through a clear window of the staging region portion 62.

In FIG. 9, the worm gear 78, in driving engagement with the gear teeth 76, causes limitated rotation of the inner ring 70, moving the dispensing chamber 102 into registration with an open portion of the dispensing aperture 62, such that the pill 60 may be deposited into the patient or other user's hands.

It can be appreciated that the reciprocating movement of the inner rings 70, caused by alternating movement of the motor 80 causes pills to singularly pass through the dispensing template 106 into the dispensing chamber 102 and to be thence moved from a staging region to a dispensing aperture of the area 62.

Figure 10:
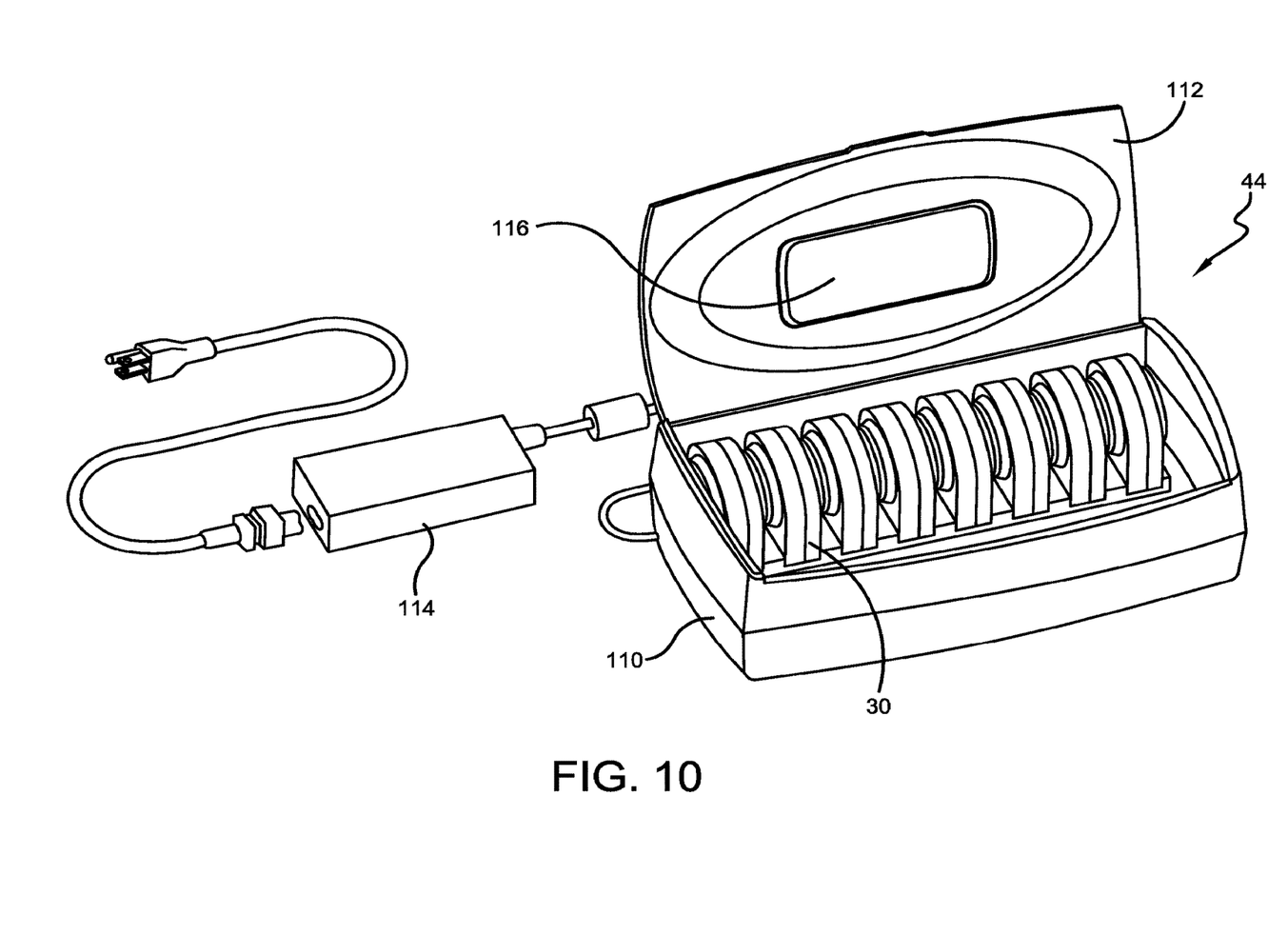
FIG. 10 is a perspective view of a docking system for personal dispensing devices.

With reference now to FIG. 10, it can be seen that the docking system 44 receives a plurality of pill dispensing devices 30, each typically having different pills or medications therein. The pill dispensing devices 30 are docked or received in an enclosure 110 of the docking system 44, which is adapted to be sealingly closed by a hinged lid 112, or the like. A power supply 114 is attached to the enclosure 110. Received within the hinged lid 112 is an appropriate communication and processing device, such as the smart phone 36, a Bluetooth, a near field communication system or any of various other types of electronic communication devices.

Figure 11:
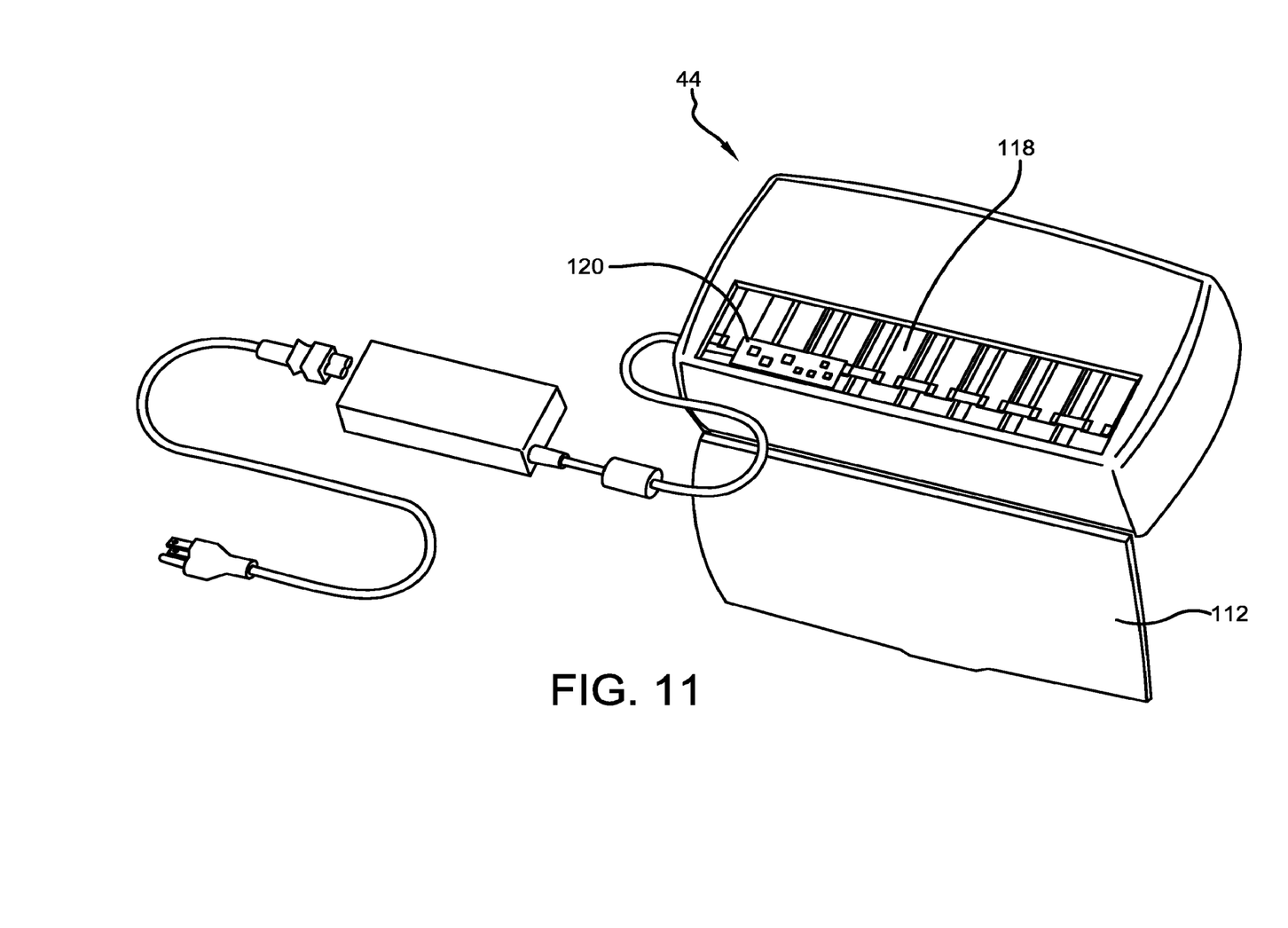
FIG. 11 is a perspective view of the docking system of FIG. 10, showing the nesting bed, pad and mother board thereof.

With reference to FIG. 11, it can be seen that the bed of the docking system 44 is adapted for receiving and mating engagement with a plurality of pill dispensing devices 30. The bed includes a near field communication printed circuit board for providing communications with the pill dispensing devices 30. Also included in the docking system 44 is a mother board 120 containing microcontroller and Bluetooth technology, as required.

With an appreciation of the basic structures employed with the apparatus and method of the invention, further attention can be given to the various details and operations thereof. As presented, the medication event monitoring system 10 consists of several hardware and software components including the use of commercially available personal electronic devices, such as smartphones, mobile tables, and the like. Alternatively, a customized personal electronic device may be employed.

The primary hardware of the system consists of the docking system 44 with a display on its inner lid 112 and a bed 118 on the floor of the docking system container. Further included are pill dispensing devices 30 that are seated in the bed of the container. A smart phone, tablet, or a customized personal electronic device 116 is received by the lid 112.

Associated with the pharmacist 16 is a programming bed, used by the pharmacist to input drug information into the pill dispensing device memory storage. The pharmacist 16 may also be provided with a label printing device to place a custom label or radio frequency identification (RFID) label on the outside of the pill dispensing device to identify the medication, if desired. Additionally, the pharmacist 16 may apply attachable sensor packages by means of adhesive or otherwise to other medication dispensing devices such as inhalers, syringes, SureClick® pens, and the like.

Various digital telemetry devices that can independently measure biomarkers, such scales for weight and body mass, oximeters, blood pressure cuffs, glucometers, and other remote monitoring systems such as monitoring components of smarthome telecare and telehelp systems may be employed in the patient center 32 and, particularly, in association with the smart house 34. Each of these systems communicate with a personal electronic device, such as the smart phone 36 uniquely associated with a patient or other individual. Of course, the nature and extent of such digital telemetry devices, meters, monitors, and the like is broad and adaptive to accommodate the needs of the patient or other individual.

Other hardware includes the use of various dispensing templates 106 to tailor the various pill dispensing devices 30 to the particular medications to be contained therein and dispensed therefrom, whether in the form of tablet, pill, capsule or the like.

Finally, a set or array of shaped beds are maintained on the floor of the docking system 44 of the closed chamber container thereof to receive the pill dispensing devices 30 to accommodate electronic communication between the pill dispensing devices 30 and the remainder of the system 10.

Software is employed in association with the medication event monitoring system 10 to control the implementation, transfer, recordation and updating of data and communications between the various pieces of hardware and individuals 12, 14 and 16 associated with its use. A control center 18 provides the heart of the operation system, residing on a server that is accessed via the internet. A reminder, monitoring, and education App resides on the smartphone or other individual electronic device 36 and is accessed via the smartphone. Microprocessor programs are associated with and operate functions of the docking system 44 while similar microprocessor programs are associated with and run the programs associated with the pill dispensing devices 30. There is software associated with the pharmacist 16 to assist in programming the pill dispensing devices 30 before they are sent as by mail 28, or the like. A multiplicity of databases of medical information also require software, such as employed by the drug databases 26*a*, 26*b*, medical education programs, psychosocial instruments, and the like.

An appreciation can now be obtained regarding the operation of the system 10, beginning with the function and operation of the docking system 44. At rest, the hinged lid 112 is closed. The software of the docking system 44, in conjunction with the coding of the pill dispensing devices 30, contains the earliest and latest time that the associated medications can be taken. If the window for taking the scheduled medications has not been entered, and the lid is opened, a display will appear on a display screen of the lid 112 with a message stating, to the effect, "No medications are to be taken at this time. The next time to take a medication is at XX:XX, X hours and X minutes from now." All of the light emitting diodes 74 on the pill dispensing devices 30 will be off. The opening of the lid 112 will be recorded in a data log and reported to the system. Of key importance is the fact that no pills can be distributed, because the pill dispensing devices are locked under program control except when the dispensing window is reached.

If the window for taking the pills has been entered, the light emitting diodes 74 on the appropriate pill dispensing device 30, containing the medication to be taken at that time, will begin flashing in a standard color, by way of example, the color green. When the patient 12 opens the lid 112 of the docking system 44, it will show on the display a picture of the medication or medications to be taken. It will show a picture of the first pill to be taken, dosages, the reason for taking the medication, warnings, and any additional information for taking the medication as, for example, whether it should be taken with a glass of water, food, or the like. The pill dispensing device 30 of interest, with the specific medication on the screen, will have its light emitting diodes 74 flashing at double the pace of those of the other pill dispensing devices 30, if there are more than one. The display can also show how to pick up the pill dispensing device 30, place it in the hand, tap and tilt it, such that the desired pill or medication drops out of the dispensing aperture 62.

Once the appropriate pill dispensing device 30 is retrieved from its nest in the bed of the docking system 44, the pill dispensing process is engaged, requiring any of a combination of orientations, motions, touches, and photo-sensing. While any of a number of combinations of sensed activity can give rise to the reciprocating operation of the motor 80, turning the inner ring 70 to move a pill to be dispensed from a staging area to a dispensing area of the dispensing aperture and window 62, various embodiments of such sensors are shown in FIG. 5, as will be readily appreciated by those skilled in the art. The temperature sensor may serve to identify the fact that the dispenser 30 is being held by the warmth of an individual. The gyroscope 90 emits a signal corresponding to orientation, while the accelerometer 92 emits a signal corresponding to motion. The outputs of these sensors are employed, along with the capacitive sensor 94 to effect the dispensing operation. When the pill dispensing device 30 is placed in the palm of the hand, the capacitive sensor 94 senses that act, interrupting the microcontroller 86 to collect data from the various sensors 88-92. When the motion, orientation and/or temperature are detected to be appropriate, the microcontroller 86 causes the motor 80 to clock, such that a pill will be moved from the closed staging chamber to the open dispensing chamber of the dispensing aperture 62, such that the pill may be dropped into the palm of the hand by gravity, or pushed out by a motor or piston type push blade. The motor will only clock if a pill is detected in the dispensing chamber 102 by the interrupting of the light source 98 and photo detector or photo diode 100. The process continues if a second or third pill is to be dispensed.

An alternative method is for the sensor to determine if a fixed vertical height and motion along one plane has been experienced while a photo-sensor at the bottom of the pill dispenser 30 senses a table top. Then, the motor clock can be triggered to dispense a pill onto the table.

It is fundamental that the pill must fall into the chamber 102, the sensors 98, 100 must detect the pill as present in the chamber, and the capacitive sensor 94 or photo-sensor on the bottom detects a hand or surface in contact and then the motion is made such as by tapping or tilting of the pill dispensing device 30. Upon the occurrence of that sequence, or any other desired sequence, the motor 80 will be caused to activate, move the pill from the staging chamber to the dispensing portion of the dispensing aperture 62 such that it will drop into the patient's hand or onto a surface.

The pill dispensing is recorded in a microprocessor contained in the docking system 44. If a second pill is required at the time, the light emitting diode 74 will continue to flash. If the last pill for that time has been dispensed, the light emitting diode will stop flashing and become solid green. The pill dispensing device 30 may then be nested back into the bed of the docking system 44.

At the distribution end of the chain, particularly as it relates to the pharmacist 16, the following process will typically occur. To begin, the pill dispensing devices 30 can be adjusted to accommodate virtually and size of shape of pill by employing the appropriate templates 106. The pill dispensing devices 30 may themselves have any of varying sizes of cavities 58, sufficient to accommodate a standard 90-day supply of very small pills such as 81 g aspirin, to a 90-day supply of very large pills such as glucosamine-chondroiten.

In a commercial pharmacy, a pharmacist 16 will typically have a supply of pill dispensing devices 30, various sizes of windows or side caps 54, 56, and various sizes and shapes of dispensing templates 106 to accommodate the wide variety of pills, tablets, capsules and the like that are contemplated. The pharmacist 16, upon receiving a request for medication, fills the personal dispensing device 30 with the appropriate medication. The side caps or windows 54, 56 are placed on the pill dispensing device 30 and that device is then place into a programming bed of the pharmacist. The programming bed is identical to the near field communication antenna bed in the docking system 44. The pharmacist 16 will typically utilize a custom database through the control center 18, or an existing drug database system to program the pill dispensing device with the information for the individual to take the medication, such as drug name, dosage, prescriber, link to warning information, consumer information sheet, and the like. Once the pill dispensing device 30 is programmed, it can be placed alone or with other pill dispensing devices 30 into a docking system 44 for initial distribution, or into an envelope or mailing box 28 to be sent to a patient or appropriate individual.

The pill dispensing devices 30 arrive in the mail to the patient 12 and can be placed in the docking system 44 already in the patient's smart home 34. If this is the first time a patient 12 is receiving the entire docking system 44, then a simple instruction sheet may tell the patient 12 to place the docking system 44 on a table or dresser, plug it in, and open the lid. The lid 112 will display a video presentation that explains the function and operation of the system 44. The lid 112 will self-register with a paired smart device such as a smart phone 36, or other communication and processing device 116. Alternatively, the docking system 44 may be configured to operate independently or through the internet (cloud) with appropriate databases 26 or licensed branded database enterprise systems 26a, 26b, and caregivers and researchers 14 and the pharmacist 16. The docking systems 44 may be distributed and set up by case managers, physicians, nurses, researchers or pharmacists. Indeed, it can be set-up by patients themselves.

With reference to the medication event monitoring system 10 of FIG. 1, it can now be further appreciated that in one or more embodiments, the system described herein is intended to improve the medication adherence and health behaviors of patients by providing real time reminders and recording medication adherence, health behavior, attitudinal, and physical health related data. In certain embodiments, the medication adherence system may include a docking system 44 that interoperates with software installed on one or more personal electronic devices 36. The docking system 44 may communicate with the personal electronic device to indicate events such as, for example, the opening and closing of the lid 112 and the accessing and using of the pill dispensing devices or containers 30 received by the docking system 44. In one or more embodiments, the personal electronic device or smartphone 36 may provide real-time reminders to users about medication taking or other health behaviors such as, for example, exercise, physical therapy, or carrying out activities in support of a clinical research trial. In certain embodiments, the smartphone 36 and/or the docking system 44 may display drug taking information upon the accessing of a pill dispensing device 36, or upon the occurrence of a reminder. In other embodiments, the smartphone 36 and/or docking system 44 may display information about chronic conditions with the intent of activating the patient through knowledge or by influencing motivation to carry out with more confidence the self-management of a chronic health or mental health condition.

As presented above, the docking system 44 may include a base and hinged lid 112 that is movable between a closed position and an open position. In one or more embodiments, the lid includes a display screen on an inner surface, the display screen being visible to a user when the lid is opened. The docking system may contain a plurality of pill dispensing devices 30. In one or more embodiments, docking system 44 may include a refrigeration unit to cool all or part of the docking system. In certain embodiments, the docking system 44 may contain a wireless router to interface with a wireless network. In one or more embodiments, the docking system may contain a sim card and GSM to connect directly to a cellular network. It may also optionally contain noise, vibration, or light generating equipment that is intended to alert an individual that an activity is required. Activities for which the docking system 44 may provides reminders may include, for example, taking medication, completing a survey, recording a physical attribute, interacting with a digital data gathering device, or carrying out an activity in support of a clinical research trial.

The pill dispensing devices 30 may also be inhalers, or other types of medication containing objects. Sensors may be provided in association with each such container capable of identifying if and when it has been accessed, indicating that medication contained therein is or will be taken. Each of the plurality of devices 36 may be provided with a unique electronic signal or identifier that may be associated with medication contained within the container. In one or more embodiments, the devices 36 may also be number, color and shape coded to aid in the identification of the correct medication device and medication.

The docking system 44 and/or devices 36 communicate with a personal electronic device 36 having medication reminder software installed thereon. In one or more embodiments, the medication reminder software may be an application or "App" available for download through one of a variety of "App" stores. The App may work independently, in conjunction with a database within the docking system 44, or in concert with a web-based or "cloud-based" management control center and data repository. The personal electronic device 36 may be any known portable electronic device, such as cell phones, smart phones, tablets, laptop computers, or digital data gathering instruments such as, for example, a wirelessly connected scale, blood pressure cuff, heart monitor, or glucose meter. In one or more embodiments, the medication adherence software may provide automated reminders regarding the scheduling of medication. The automated reminders may include the name of the medication, the dosage, medication instructions, a picture, warnings, and other relevant details, and optionally a number, shape and/or color indicating the correct pill dispensing device 30 within docking system 44. In one or more embodiments, a speaker or buzzer may be provided to provide audio cues of the same information. The medication adherence software may include a drug page or tab linked to a drug database, thereby providing users with access to drug information, as needed.

In certain embodiments, the opening and/or closing of the lid 112 of the docking system 44 and the accessing and/or closing of the plurality of devices 30 may be communicated to the personal electronic device 36. The device 36 and/or a display screen on the lid 112 may display the associated drug information for the accessed device 36. This display may include a photograph of the drug or medication, the correct dosage, instructions for taking the medication, etc. In certain embodiments, the use of the devices 30 and docking system 44 may be time and date stamped for recording purposes.

The personal electronic device 36 and/or display screen of the lid 112 may also provide daily medication summaries, and may allow for other health related reminders, summaries, or educational materials all under software control. In certain embodiments, the device 36 and system 44 software may record the opening and/or closing of the lid 112 and activation of the devices 30, and may provide reporting functions to monitor the adherence to prescribed medication schedules. In certain embodiments, the docking system 44 and/or personal electronic device 36 may provide a notification or warning that a pill dispensing device 30 has not be returned to the docking system 44 after a predetermined period of time.

The docking system 44 and/or pill dispensing devices 30 may communicate with the personal electronic device 36 and the medication adherence software by any known wireless communication protocol. For example, WiFi, radio frequency, Bluetooth, and ZigBy may be employed to provide such wireless communication.

Thus it can be seen that various aspects of embodiments of the invention have been presented and described herein. While in accordance with the patent statutes only the best mode and preferred embodiments of the invention have been presented and described in detail, it will be appreciated that the invention is not limited thereto or thereby. Accordingly, for an appreciation of the true scope and breadth of the invention, reference should be made to following claims.

What is claimed is:

1. A pill dispensing device, comprising:
   a housing defining a bulk pill cavity therein;
   a dispensing aperture in said housing, said dispensing aperture having a staging region for holding a pill and an open portion for dispensing a pill to a user;
   a dispensing chamber providing selective communication between said bulk pill cavity and said dispensing aperture; and
   sensors detecting attitudes from among motion, position or orientation of the pill dispensing device, wherein said dispensing chamber receives a pill from said bulk pill cavity and wherein said dispensing chamber holds said pill in said staging region of said dispensing aperture until said sensors detect one or more of motion, position or orientation of the pill dispensing device, and upon such detecting, a dispensing operation begins such that said pill is moved from said staging region of said dispensing aperture to said open portion of said dispensing aperture.

2. The pill dispensing device as recited in claim 1, wherein said dispensing chamber includes a dispensing template sized and configured to allow for said pill to move from said bulk pill cavity into said dispensing chamber.

3. The pill dispensing device as recited in claim 1, wherein said sensors include an accelerometer, a gyroscope, and a magnetometer.

\* \* \* \* \*